United States Patent
Idoji et al.

(10) Patent No.: US 8,697,701 B2
(45) Date of Patent: Apr. 15, 2014

(54) SOLID GERMICIDAL COMPOSITION AND DISINFECTION METHOD

(71) Applicant: Ueno Fine Chemicals Industry, Ltd., Osaka (JP)

(72) Inventors: Hiroki Idoji, Osaka (JP); Ayako Tsurusaki, Osaka (JP); Shigeyuki Suginaka, Osaka (JP); Futoshi Maeda, Osaka (JP); Yoshiaki Kuriyama, Osaka (JP)

(73) Assignee: Ueno Fine Chemicals Industry, Ltd., Osaka (JP)

( * ) Notice: Subject to any disclaimer, the term of this patent is extended or adjusted under 35 U.S.C. 154(b) by 0 days.

(21) Appl. No.: 13/954,154

(22) Filed: Jul. 30, 2013

(65) Prior Publication Data

US 2014/0039023 A1    Feb. 6, 2014

(30) Foreign Application Priority Data

Jul. 31, 2012   (JP) .................................. 2012-169529

(51) Int. Cl.
*A01N 31/00*   (2006.01)
*A61K 31/70*   (2006.01)
(52) U.S. Cl.
CPC ...................................... *A61K 31/70* (2013.01)
USPC .................................................... 514/252.16
(58) Field of Classification Search
None
See application file for complete search history.

(56) References Cited

U.S. PATENT DOCUMENTS 5,620,595 A    4/1997    Austin et al.

FOREIGN PATENT DOCUMENTS

| KR | 10-2012-0074688 A | 7/2012 |
| WO | 01/74987 A1 | 10/2001 |
| WO | 2012/148004 A1 | 11/2012 |

OTHER PUBLICATIONS

Choi, N-S., et al. Electrochimica Acta, 56 (2011) 7249-7255.*
"Practical Data Collection regarding Disinfection of Microorganisms", Science Forum Inc, Aug. 11, 2005, pp. 130-132.
Extended European Search Report for Application No. 13178540.4 dated Nov. 25, 2013.
Database WPI Week 201224 Thomson Scientific, London, GB; AN 2012-B52571 XP-002716199 for CN 102 308 849 A (Jan. 11, 2012).

* cited by examiner

*Primary Examiner* — San-Ming Hui
*Assistant Examiner* — Jeanmarie Calvillo
(74) *Attorney, Agent, or Firm* — Sughrue Mion, PLLC

(57) ABSTRACT

A solid germicidal composition containing a compound of the formula (I), a carbonate compound and an organic acid with a solubility in water at 20° C. of 0.25 to 35%:

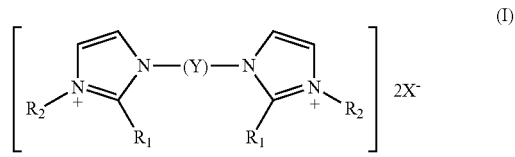

wherein, $R_1$ represents a saturated linear alkyl group having 1 to 3 carbon atoms, $R_2$ represents a saturated linear alkyl group having 8 to 12 carbon atoms, $X^-$ represents a halogen ion and Y represents a saturated linear alkylene group having 8 to 12 carbon atoms is disclosed. A method for disinfecting an object, which comprises contacting an aqueous solution of the composition with the object, is also disclosed. The solid germicidal composition is effective against various microorganisms and hardly causes development of resistance to the composition itself in microorganisms even when the composition is continually or continuously used.

10 Claims, No Drawings

SOLID GERMICIDAL COMPOSITION AND DISINFECTION METHOD

TECHNICAL FIELD

The present invention relates to a solid germicidal composition which is mainly used for disinfection of floors, walls, tools, facilities and the like in, for example, food factories, and a disinfection method using such composition.

BACKGROUND ART

At places where food is handled, such as food factories, kitchens in restaurants and processing workshops in grocery stores, disinfection of floors, walls, tools, facilities and the like is required. Various germicides have been hitherto used such as alcohols, chlorinated compounds, peroxides, cationic surfactants, amphoteric surfactants and biguanide compounds. For example, didecyl dimethyl ammonium chloride and polyhexamethylene biguanide hydrochloride are safe and effective germicides and are frequently used.

Microorganisms resistant to quaternary ammonium salts and biguanide germicides (hereinafter also referred to as "drug-resistant microorganisms") have been developed in the course of repeated use of these germicides and cause insufficient disinfection. For example, as described in Non-Patent Document 1, bacteria of genus *Pseudomonas* and genus *Serratia* are known as microorganisms resistant to didecyl dimethyl ammonium chloride and polyhexamethylene biguanide hydrochloride. Although the types of germicides used for the disinfection may periodically be changed in order to prevent the development of drug-resistance in microorganisms, frequent change of germicides causes low working efficiency and high costs. Drug-resistant microorganisms are usually treated by chlorinated germicides such as sodium hypochlorite. The chlorinated germicides, however, cause corrosion and damages on facilities and devices, and also cause unfavorable residual odor. Sliminess is prone to remain after using didecyl dimethyl ammonium chloride. Stickiness is prone to remain after using polyhexamethylene biguanide hydrochloride.

Germicides comprising didecyl dimethyl ammonium chloride and polyhexamethylene biguanide hydrochloride have been provided in the form of liquid preparation. In general, liquid germicidal compositions are provided in the form of concentrated solution that is diluted upon use. However, a lot of time is required for dilution. When the concentration of the solution is incorrectly adjusted, there is a possibility that germicidal effect will not be exerted or irritation to the skin or the like will occur. Meanwhile, if a germicidal composition can be provided in the form of solid preparation, its concentration can be accurately and easily adjusted. The solid composition can contribute to the downsizing and weight reduction of products, improvements in working efficiency such as saving in storage area, the reduction of packaging materials and the lowering of transporting costs.

From the circumstances as described above, desired germicidal composition is a solid composition which has germicidal effects on fungi such as mold and on general bacteria as well as on drug-resistant microorganisms, hardly causes development of drug-resistance in microorganisms even when the composition is continually or continuously used and remains less slimy and less sticky after using the composition.

PRIOR ART DOCUMENT

Non-Patent Document

[Non-Patent Document 1] Practical data collection regarding disinfection of microorganisms (published on Aug. 11, 2005, Science Forum Inc.)

SUMMARY OF THE INVENTION

An object of the present invention is to provide a solid germicidal composition, which has germicidal effects on fungi and general bacteria and also has germicidal effects on microorganisms resistant to quaternary ammonium salts such as didecyl dimethyl ammonium chloride as well as on microorganisms resistant to biguanide germicides such as polyhexamethylene biguanide hydrochloride, and hardly causes development of resistance to the composition in microorganisms.

The present inventors have found that the above problems can be solved by a composition containing a compound of the following formula (I), a carbonate compound and a specific organic acid, and then completed the present invention.

The present invention provides a solid germicidal composition containing a compound of formula (I), a carbonate compound and an organic acid with a solubility in water at 20° C. of 0.25 to 35%:

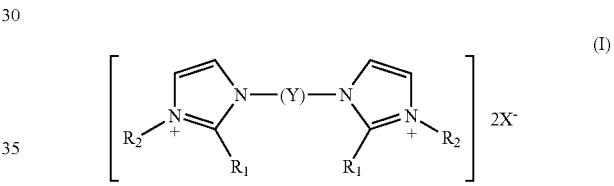

wherein, $R_1$ represents a saturated linear alkyl group having 1 to 3 carbon atoms, $R_2$ represents a saturated linear alkyl group having 8 to 12 carbon atoms, $X^-$ represents a halogen ion and Y represents a saturated linear alkylene group having 8 to 12 carbon atoms.

The present invention also provides a method for disinfecting an object, which comprises contacting an aqueous solution of the solid germicidal composition with the object.

The present invention further provides use of an aqueous solution of the solid germicidal composition as a germicide.

The solid germicidal composition of the present invention has germicidal effects on fungi such as molds and general bacteria and also has excellent germicidal effects on drug-resistant microorganisms resistant to quaternary ammonium salts and/or biguanide germicides. Even when the composition is continually or continuously used for a long period of time, the composition hardly causes development of resistance to the composition itself in microorganisms. In addition, less sliminess and less stickiness remain after using the solid germicidal composition of the present invention as compared to the case where quaternary ammonium salts or biguanide germicides is used. The solid germicidal composition of the present invention is provided as a solid preparation and therefore, its concentration can be accurately and easily adjusted upon use. The composition exerts effects such as the downsizing and weight reduction of products, improvements in working efficiency such as saving in storage area, the reduction of packaging materials and the lowering the transporting costs.

DETAILED DESCRIPTION OF THE INVENTION

In the compound of the formula (I), $R_1$ is a methyl group, an ethyl group or a propyl group, preferably a methyl group or an ethyl group, and more preferably a methyl group. $R_2$ is a saturated linear alkyl group having 8 to 12 carbon atoms, preferably a saturated linear alkyl group having 8 to 10 carbon atoms, and more preferably a decyl group. $X^-$ is a halogen ion, preferably a chloride ion or a bromide ion, and more preferably a chloride ion. Y is a saturated linear alkylene group having 8 to 12 carbon atoms, preferably a saturated linear alkylene group having 10 to 12 carbon atoms, and more preferably a decylene group.

Specific examples of the compound of the formula (I) include 1,10-di(3-decyl-2-methylimidazolium)decane dibromide, 1,10-di(3-decyl-2-methylimidazolium)decane dichloride, 1,12-di(3-decyl-2-methylimidazolium)dodecane dibromide, 1,12-di(3-decyl-2-methylimidazolium)dodecane dichloride, 1,10-di(3-octyl-2-methylimidazolium)decane dibromide, 1,10-di(3-octyl-2-methylimidazolium)decane dichloride, 1,12-di(3-octyl-2-methylimidazolium)dodecane dibromide and 1,12-di(3-octyl-2-methylimidazolium)dodecane dichloride. Among these, 1,10-di(3-decyl-2-methylimidazolium)decane dibromide, 1,10-di(3-decyl-2-methylimidazolium)decane dichloride, 1,12-di(3-decyl-2-methylimidazolium)dodecane dibromide, 1,12-di(3-decyl-2-methylimidazolium)dodecane dichloride, 1,12-di(3-octyl-2-methylimidazolium)dodecane dibromide and 1,12-di(3-octyl-2-methylimidazolium)dodecane dichloride are preferred in terms of germicidal effects on general bacteria. When other germicidal ingredients such as a quaternary ammonium salt, a biguanide germicide and an organic iodine germicide are contained in the solid germicidal composition of the present invention, 1,10-di(3-decyl-2-methylimidazolium)decane dibromide, 1,10-di(3-decyl-2-methylimidazolium)decane dichloride, 1,12-di(3-decyl-2-methylimidazolium)dodecane dichloride and 1,12-di(3-octyl-2-methylimidazolium)dodecane dichloride are more preferred in terms of good compatibility with the other germicidal ingredients, and 1,10-di(3-decyl-2-methylimidazolium)decane dichloride is further preferred in terms of germicidal effects on drug-resistant microorganisms and solubility in water.

The total amount of the compound of the formula (I) in the solid germicidal composition of the present invention is not particularly limited, and is preferably 1 to 90% by weight, more preferably 3 to 80% by weight and even more preferably 5 to 60% by weight relative to the whole amount of the solid germicidal composition.

In the present invention, the carbonate compound is one or more compounds selected from the group consisting of carbonates, bicarbonates and double salts thereof. Carbonates may include sodium carbonate, calcium carbonate, potassium carbonate and magnesium carbonate. Bicarbonates may include sodium bicarbonate and potassium bicarbonate. Double salts may include sodium sesquicarbonate. Among these carbonate compounds, sodium bicarbonate and sodium carbonate are preferred because they have excellent solubility in water. Two or more carbonate compounds may be used in combination.

The total amount of the carbonate compound in the solid germicidal composition of the present invention is not particularly limited insofar as the solid germicidal composition can be dissolved in water. The total amount of the carbonate compound is preferably 0.05 to 18 parts by weight, more preferably 0.2 to 15 parts by weight, and further preferably 0.4 to 11 parts by weight relative to 1 part by weight of the compound of the formula (I). When the total amount of the carbonate compound is less than 0.05 parts by weight relative to 1 part by weight of the compound of the formula (I), the organic acid in the solid germicidal composition tends to remain undissolved. When the total amount of the carbonate compound is more than 18 parts by weight relative to 1 part by weight of the compound of the formula (I), the carbonate compound tends to remain undissolved.

In the present invention, the organic acid has a solubility in water at 20° C. of 0.25 to 35%. The solubility of the organic acid in water at 20° C. is preferably 0.5 to 30%, more preferably 0.7 to 25%, and further preferably 1.0 to 15%. When an organic acid with a solubility in water at 20° C. of less than 0.25% is used, the solubility of the solid germicidal composition in water tends to be lowered. When an organic acid with a solubility in water at 20° C. of more than 35% is used, tabletting problems such as sticking and capping tend to occur when producing tablets. Examples of the organic acid with a solubility in water at 20° C. of 0.25 to 35% which can be used in the present invention include succinic acid, adipic acid, fumaric acid, benzoic acid and ascorbic acid, and succinic acid and adipic acid are preferable. Hereinafter, "an organic acid with a solubility in water at 20° C. of X %" is also simply referred to as "an organic acid with a solubility of X %" for convenience.

The total amount of the organic acid in the solid germicidal composition of the present invention is preferably 0.05 to 18 parts by weight, more preferably 0.2 to 15 parts by weight and further preferably 0.4 to 11 parts by weight relative to 1 part by weight of the compound of the formula (I). When the total amount of the organic acid is less than 0.05 parts by weight relative to 1 part by weight of the compound of the formula (I), the carbonate compound in the solid germicidal composition tends to remain undissolved. When the total amount of the organic acid is more than 18 parts by weight relative to 1 part by weight of the compound of the formula (I), a germicidal activity tends to be decreased.

An additional germicidal ingredient can be incorporated into the solid germicidal composition of the present invention. Examples of the additional germicidal ingredients which can be incorporated into the solid germicidal composition of the present invention include quaternary ammonium salts such as didecyl dimethyl ammonium chloride and benzalkonium chloride; biguanide germicides such as polyhexamethylene biguanide hydrochloride and chlorhexidine gluconate; and organic iodine germicides such as an iodine-glycine complex. Two or more of these germicidal ingredients may be used in combination.

When the additional germicidal ingredients are incorporated into the solid germicidal composition of the present invention, the total amount of the additional germicidal ingredients is preferably 0.5 to 40 parts by weight, more preferably 0.7 to 10 parts by weight and further preferably 1 to 5 parts by weight relative to 1 part by weight of the compound of the formula (I). When the total amount of the additional germicidal ingredients is less than 0.5 parts by weight relative to 1 part by weight of the compound of the formula (I), germicidal effects by the additional germicidal ingredients do not tend to be sufficiently exerted. When the total amount of the additional germicidal ingredients is more than 40 parts by weight relative to 1 part by weight of the compound of the formula (I), white turbidity tends to be yielded in the aqueous solution of the solid germicidal composition.

Additives can be further incorporated into the solid germicidal composition of the present invention as needed. Examples of the additives which can be incorporated into the solid germicidal composition include excipients, coloring agents, perfumes, binding agents, disintegrators and lubricants. As the excipients, for example, dextrin, cellulose derivatives and lactose can be used. The total amount of these other additives in the solid germicidal composition of the present invention is usually 50% by weight or less relative to the whole amount of the solid germicidal composition.

The solid germicidal composition of the present invention is a solid preparation. Dosage form of the composition may preferably be powders, particles, granules or tablets but is not limited to these forms.

The solid germicidal composition of the present invention can be obtained by simply mixing, together with excipients if needed, required ingredients, and can also be further subjected to common drug formulation processes such as granulation and tabletting.

Examples of the solid germicidal composition of the present invention include:
(A) a composition containing the compound of the formula (I), 0.05 to 18 parts by weight of the carbonate compound relative to 1 part by weight of the compound of the formula (I) and 0.05 to 18 parts by weight of the organic acid with a solubility of 0.25 to 35% relative to 1 part by weight of the compound of the formula (I);
(B) a composition containing the compound of the formula (I), 0.2 to 15 parts by weight of the carbonate compound relative to 1 part by weight of the compound of the formula (I) and 0.2 to 15 parts by weight of the organic acid with a solubility of 0.25 to 35% relative to 1 part by weight of the compound of the formula (I);
(C) a composition containing the compound of the formula (I), 0.4 to 11 parts by weight of the carbonate compound relative to 1 part by weight of the compound of the formula (I) and 0.4 to 11 parts by weight of the organic acid with a solubility of 0.25 to 35% relative to 1 part by weight of the compound of the formula (I); and
(D) a composition containing 1 to 90% by weight of the compound of the formula (I), 2.5 to 90.25% by weight of the carbonate compound and 2.5 to 90.25% by weight of the organic acid with a solubility of 0.25 to 35%.

Examples of the solid germicidal composition of the present invention further comprising other germicidal ingredient include:
(E) a composition containing the compound of the formula (I), 0.05 to 18 parts by weight of the carbonate compound relative to 1 part by weight of the compound of the formula (I), 0.05 to 18 parts by weight of the organic acid with a solubility of 0.25 to 35% relative to 1 part by weight of the compound of the formula (I) and 0.5 to 50 parts by weight of polyhexamethylene biguanide hydrochloride relative to 1 part by weight of the compound of the formula (I);
(F) a composition containing the compound of the formula (I), 0.2 to 15 parts by weight of the carbonate compound relative to 1 part by weight of the compound of the formula (I), 0.2 to 15 parts by weight of the organic acid with a solubility of 0.25 to 35% relative to 1 part by weight of the compound of the formula (I) and 0.7 to 10 parts by weight of polyhexamethylene biguanide hydrochloride relative to 1 part by weight of the compound of the formula (I);
(G) a composition containing the compound of the formula (I), 0.4 to 11 parts by weight of the carbonate compound relative to 1 part by weight of the compound of the formula (I), 0.4 to 11 parts by weight of the organic acid with a solubility of 0.25 to 35% relative to 1 part by weight of the compound of the formula (I) and 1 to 5 parts by weight of polyhexamethylene biguanide hydrochloride relative to 1 part by weight of the compound of the formula (I); and
(H) a composition containing 1 to 60% by weight of the compound of the formula (I), 2.5 to 90% by weight of the carbonate compound, 2.5 to 90% by weight of the organic acid with a solubility of 0.25 to 35% and 0.5 to 85% by weight of polyhexamethylene biguanide hydrochloride.

In order to disinfect an object using the solid germicidal composition of the present invention, usually, an aqueous solution of the composition is contacted with an object to be disinfected. The amount of water in which the solid germicidal composition is to be dissolved can be appropriately determined depending on the constituents of the composition and the degree of desired germicidal effects. For example, when a solid germicidal composition in the form of tablet which comprises 50% by weight of the compound of the formula (I) is used, an aqueous solution obtained by dissolving 4 g of the tablet in 4 to 20 L of water can be contacted with an object to be disinfected. The way of contact is not particularly limited. An aqueous solution of the solid germicidal composition of the present invention can be contacted with an object to be disinfected by common methods such as sprinkling, spraying, immersion and wiping.

Examples of the aqueous solution of the solid germicidal composition of the present invention suitable to be contacted with an object to be disinfected include:
(a) an aqueous solution of a solid germicidal composition containing the compound of the formula (I), 0.05 to 18 parts by weight of the carbonate compound relative to 1 part by weight of the compound of the formula (I) and 0.05 to 18 parts by weight of the organic acid with a solubility of 0.25 to 35% relative to 1 part by weight of the compound of the formula (I);
(b) an aqueous solution of a solid germicidal composition containing a compound of the formula (I), 0.05 to 18 parts by weight of a carbonate compound relative to 1 part by weight of the compound of the formula (I) and 0.05 to 18 parts by weight of an organic acid with a solubility of 0.25 to 35% relative to 1 part by weight of the compound of the formula (I), wherein the concentration of the compound of the formula (I) in the aqueous solution is 0.01 to 18% by weight; and
(c) an aqueous solution of a solid germicidal composition containing the compound of the formula (I), 0.2 to 15 parts by weight of the carbonate compound relative to 1 part by weight of the compound of the formula (I) and 0.2 to 15 parts by weight of the organic acid with a solubility of 0.25 to 35% relative to 1 part by weight of the compound of the formula (I), wherein the concentration of the compound of the formula (I) in the aqueous solution is 0.01 to 18% by weight.

The time during which the aqueous solution of the solid germicidal composition of the present invention is contacted with an object to be disinfected is not particularly limited, and can be appropriately determined depending on the concentrations of active ingredients. For example, when the above aqueous solution (b) is contacted with an object at normal temperature, a sufficient germicidal effect can be usually obtained by the contact for 30 seconds to 10 minutes, preferably for 1 to 5 minutes.

The water in which the solid germicidal composition of the present invention is dissolved to prepare an aqueous solution which is to be contacted with an object to be disinfected may be any of purified water such as ion exchanged water and distilled water, tap water and natural water such as ground water and underflow water, and is preferably purified water in terms of lower content of chlorine and metal ions.

The aqueous solution of the solid germicidal composition of the present invention usually has a pH range of 4.5 to 8 when the concentration of the composition in the aqueous solution is 1% by weight. The pH of the aqueous solution may be adjusted using an alkaline agent if desired. When the pH of the aqueous solution of the solid germicidal composition of the present invention is adjusted, the timing for pH adjustment is not particularly limited. An alkaline agent can be usually added to the aqueous solution of the solid germicidal composition. Alternatively, the amount of the alkaline agent by which the aqueous solution of the solid germicidal composition is adjusted to a desired pH range is determined in advance, and then, the solid germicidal composition may be dissolved in the aqueous solution in which such amount of alkaline agent is dissolved, or pH may be adjusted by directly incorporating such amount of alkaline agent into the solid germicidal composition.

The alkaline agent which can be used in the solid germicidal composition of the present invention or the aqueous solution of the composition is not particularly limited insofar as the alkaline agent does not cause changes such as precipitation and white turbidity in the aqueous solution of the solid germicidal composition. Examples of the alkaline agent include sodium hydroxide, potassium hydroxide, sodium carbonate, potassium carbonate, sodium bicarbonate, potassium bicarbonate, sodium sesquicarbonate, sodium metasilicate, sodium sesquisilicate, sodium orthosilicate, sodium orthophosphate, sodium pyrophosphate, sodium tripolyphosphate, sodium tetraphosphate, and sodium hexametaphosphate. Among these alkaline agents, sodium hydroxide and potassium hydroxide are preferred in terms of germicidal effects. Two or more of these alkaline agents may be used in combination.

The solid germicidal composition of the present invention is useful for disinfection of facilities in which food is handled, such as food factories, hospitals, barns, hotels, restaurants, schools and stores (e.g., floors, walls, ceilings, working tables, etc. of the facilities). The composition is also useful for disinfection of objects for food-related uses such as apparatuses for food production and/or processing and tools used in, for example, food factories. The apparatuses for food production and/or processing may include a variety of stirrers, mixers, homogenizers and automatic cutters. The tools may include chopping boards, kitchen knives, tableware, containers for food and dish towels.

The solid germicidal composition of the present invention has germicidal effects on fungi such as molds and general bacteria, and also exerts a germicidal activity on microorganisms resistant to quaternary ammonium salts and/or biguanide germicides, for example, microorganisms resistant to didecyl dimethyl ammonium chloride and/or polyhexamethylene biguanide hydrochloride. Therefore, the solid germicidal composition of the present invention is particularly useful as a solid germicidal composition applied to an object in or on which microorganisms resistant to quaternary ammonium salts and/or biguanide germicides exist.

Even when the solid germicidal composition of the present invention is used over a long period of time, the composition hardly causes development of drug-resistance in microorganisms as compared to the case where quaternary ammonium salts and/or biguanide germicides are used. Therefore, the solid germicidal composition of the present invention is also useful as a solid germicidal composition applied to an object to which quaternary ammonium salts and/or biguanide germicides are being applied or were previously applied.

Examples of the microorganisms resistant to quaternary ammonium salts and/or biguanide germicides include microorganisms of genus *Pseudomonas* and microorganisms of genus *Serratia*, such as *Serratia marcescens* and *Serratia liquefaciens*.

The solid germicidal composition of the present invention is suitable for continuous or continual use. Specifically, even when the solid germicidal composition of the present invention is continuously or continually used over a long period of time, the composition hardly causes development of resistance to the composition in microorganisms. More specifically, the solid germicidal composition of the present invention is characterized in that when the composition is repeatedly applied to the same object, fewer microorganisms resistant to the composition develop as compared to the case where a quaternary ammonium salt and/or a biguanide germicide is repeatedly applied in the same manner. As used herein, the expression "repeatedly applied to the same object" means that the same composition is applied multiple times (e.g., 2, 3, 4, 5, 6, 7 and 8 times or more) to the same object, or to the same microorganism species when the microorganism species to be disinfected is defined. The "continuous use" means that the same composition is consecutively used twice or more, for example, in the following manner: (Composition A, Composition A, Composition A, . . . ). The "continual use" means that the same composition is not consecutively used twice or more, but different compositions are sequentially used and the application of the same composition to the same object is continued. For example, when compositions are used in the following manner: (Composition A, Composition B, Composition C, Composition A, Composition D, . . . ), Composition A is used not continuously but continually.

EXAMPLES

The present invention is further described below by way of Examples.

Examples 1 to 7 and Comparative Examples 1 to 4

Tabletting Test

Raw materials were mixed according to the formulations shown in Table 1, and stability at one hour after the mixing was confirmed at room temperature. Tablets were produced by directly compressing 0.2 g of the mixed raw materials using a continuous tabletting machine (Piccola B-10, manufactured by RIVA Ltd.) under tabletting conditions of a punch (φ8 mm, R 12 mm) and compression pressure of 1 kN, and tabletting properties were observed. With respect to the formulations by which tablets could be produced, tablet hardness was measured and the state of the aqueous solutions obtained by dissolution of the tablets was observed.

(Stability)

The rating "o (circle)" indicates that the conditions of raw materials just after mixing were not changed. The rating "x (cross)" indicates that the raw materials caked by moisture absorption.

(Tabletting Properties)

Tablets with a smooth surface and a gloss were rated as "o (circle)". The rating "Δ (triangle)" represents the tablets in which sticking occurred. The rating "x (cross)" indicates that capping occurred and tablets could not be produced.

(Tablet Hardness)

The tablet hardness was measured by applying a load on the tablet in diametrical direction using Kiya's digital hardness tester (KHT-20N type, manufactured by FUJIWARA SCIENTIFIC CO., LTD.).

(State of Aqueous Solution)

A tablet was put in 200 ml of water at 20° C., and the state of the aqueous solution was observed after completion of foaming.

The solid germicidal composition of the present invention showed excellent results in terms of stability, tabletting properties, tablet hardness and the state of aqueous solution after dissolution. The results are shown in Table 2.

TABLE 1

| Ingredient (wt %) | Example 1 | Example 2 | Example 3 | Example 4 | Example 5 | Example 6 | Example 7 | Comparative Example 1 | Comparative Example 2 | Comparative Example 3 | Comparative Example 4 |
|---|---|---|---|---|---|---|---|---|---|---|---|
| Germicidal ingredient A *1 | 50 | 50 | 50 | 50 | 50 | 50 | 50 | 50 | 50 | 50 | 0 |
| PHMB *2 | 0 | 0 | 0 | 0 | 0 | 0 | 0 | 0 | 0 | 0 | 50 |
| Sodium bicarbonate | 25 | 0 | 25 | 0 | 25 | 0 | 0 | 25 | 25 | 25 | 25 |
| Sodium carbonate | 0 | 25 | 0 | 25 | 0 | 25 | 0 | 0 | 0 | 0 | 0 |
| Potassium carbonate | 0 | 0 | 0 | 0 | 0 | 0 | 25 | 0 | 0 | 0 | 0 |
| Succinic acid (solubility 6.45%) | 25 | 25 | 0 | 0 | 0 | 0 | 0 | 0 | 0 | 0 | 25 |
| Adipic acid (solubility 1.78%) | 0 | 0 | 25 | 25 | 0 | 0 | 0 | 0 | 0 | 0 | 0 |
| Fumaric acid (solubility 0.51%) | 0 | 0 | 0 | 0 | 25 | 25 | 25 | 0 | 0 | 0 | 0 |
| Citric acid (solubility 73%) | 0 | 0 | 0 | 0 | 0 | 0 | 0 | 25 | 0 | 0 | 0 |
| Malic acid (solubility 55.8%) | 0 | 0 | 0 | 0 | 0 | 0 | 0 | 0 | 25 | 0 | 0 |
| Tartaric acid (solubility 58%) | 0 | 0 | 0 | 0 | 0 | 0 | 0 | 0 | 0 | 25 | 0 |
| pH (1 wt % aqueous solution) | 5.9 | 6.5 | 6.9 | 6.6 | 6.4 | 7.3 | 5.6 | 6.4 | 6.5 | 6.4 | 5.0 |

*1 Germicidal ingredient A: 1,10-di(3-decyl-2-methylimidazolium)decane dichloride (10-10-10-Cl)
*2 PHMB: polyhexamethylene biguanide hydrochloride
In the table, the solubility values of organic acids represent solubility in water at 20° C.

TABLE 2

| | Example 1 | Example 2 | Example 3 | Example 4 | Example 5 | Example 6 | Example 7 | Comparative Example 1 | Comparative Example 2 | Comparative Example 3 | Comparative Example 4 |
|---|---|---|---|---|---|---|---|---|---|---|---|
| Stability | ○ | ○ | ○ | ○ | ○ | ○ | ○ | x | x | x | ○ |
| Tabletting properties | ○ | ○ | Δ | Δ | ○ | ○ | ○ | x | x | x | ○ |
| Tablet hardness (N) | 27.0 | 18.0 | 26.0 | 20.0 | 24.6 | 18.2 | 31.5 | | | | 20.0 |
| State of aqueous solution | clear | clear | clear | clear | clear with undissolved residues | clear with undissolved residues | white turbid with undissolved residues | | | | clear |

Germicidal Activity Test

With respect to the formulations of Examples 1 to 7 and Comparative Examples 4 in which tablets could be produced without the occurrence of capping in the tabletting test, tablets were produced in the same conditions and manner as described in the tabletting test except that 0.15 g of mixed raw materials was subjected to tabletting. The obtained tablets were dissolved in sterile water to obtain 15 g of aqueous solution (the concentration of the solid germicidal composition in the aqueous solution is 1.0% by weight).

(Drug-Resistant Bacteria)

The following sample bacterium (i) isolated from a food factory was cultured in a BHI bouillon medium at 30° C. for 24 hours. A 0.03 ml of a liquid obtained by diluting the cultured bacterium with a physiological saline solution to the concentration on the order of $10^6$ cfu/ml was mixed with respective 3 ml of aqueous solutions, each of which was obtained by diluting an aqueous solution of the above solid germicidal composition (1.0% by weight) with sterile water so that the concentration of the solid germicidal composition would be 0.01, 0.02 and 0.04% by weight, respectively. The obtained mixture was then left at 25° C. for 5 minutes. After sensitization time elapsed, stirring was carried out again. One platinum loop of each mixture was taken and inoculated in 10 ml of a BHI bouillon medium. The medium was incubated at 30° C. for 48 hours. A BHI bouillon medium without inoculation of the bacterium was used as a reference, and turbidity of the medium was compared with the reference by visual inspection to determine the germicidal effect of the aqueous solution of the solid germicidal composition on the bacterium. In a preliminary test, the proliferation of the following sample bacterium (i) was not inhibited even when the treatment with didecyl dimethyl ammonium chloride at a maximum concentration of up to 80 ppm or with polyhexamethylene biguanide hydrochloride at a maximum concentration of up to 320 ppm (sensitization time 5 minutes) was carried out, and therefore, the sample bacterium (i) was confirmed to be resistant to these compounds.

Sample Bacterium (i): *Serratia marcescens* (Bacterium 1 Isolated from a Food Factory)

(Mold)

A 0.03 ml of liquid obtained by diluting a spore suspension of the following sample bacterium (ii) with a physiological saline solution to the concentration on the order of $10^6$ cfu/ml was mixed with respective 3 ml of aqueous solutions, each of which was obtained by diluting an aqueous solution of the above solid germicidal composition (1.0% by weight) with sterile water so that the concentration of the solid germicidal composition would be 0.04 and 0.08% by weight, respectively. The obtained mixture was then left at 25° C. for 5 minutes. After sensitization time elapsed, stirring was carried out again. One platinum loop of each mixture was taken and inoculated in 10 ml of a BHI bouillon medium. The medium was incubated at 30° C. for 120 hours. A BHI bouillon medium without inoculation of the bacterium was used as a reference, and turbidity of the medium was compared with the reference by visual inspection to determine the germicidal effect of the aqueous solution of the solid germicidal composition.

Sample Bacterium (ii): *Aspergillus niger* ATCC16404

The solid germicidal composition of the present invention exerted an excellent germicidal activity on drug-resistant bacteria and molds. The results are shown in Tables 3 and 4. In the tables, the "+" represents that the proliferation of the microorganism was observed, and the "−" represents that the proliferation of the microorganism was not observed.

factured by RIVA Ltd.) under tabletting conditions of punch ($\phi$8 mm, R 12 mm) and compression pressure of 1 kN. Then, under the following conditions, tablet hardness and dissolution time were determined and the state of the aqueous solution obtained by dissolution of the tablet was observed. The results are shown in Table 6.

(Tablet Hardness)

The tablet hardness was measured by applying a load on the tablet in diametrical direction using Kiya's digital hardness tester (KHT-20N type, manufactured by FUJIWARA SCIENTIFIC CO., LTD.).

TABLE 3

*Serratia marcescens* (bacterium 1 isolated from a food factory) $1.3 \times 10^6$ cfu/ml

| Concentration | Example 1 | | | Example 2 | | | Example 3 | | | Example 4 | | | Example 5 | | | Example 6 | | | Example 7 | | | Comparative Example 4 | | |
|---|---|---|---|---|---|---|---|---|---|---|---|---|---|---|---|---|---|---|---|---|---|---|---|---|
| 0.04% | − | − | − | − | − | − | − | − | − | − | − | − | − | − | − | − | − | − | − | − | − | + | + | + |
| 0.02% | + | − | − | + | − | − | + | − | − | + | − | − | − | − | − | + | − | − | − | − | − | + | + | + |
| 0.01% | + | + | − | + | + | − | + | − | − | + | + | + | + | + | + | + | − | − | + | + | + | + | + | + |
| Contact time (min) | 1 | 3 | 5 | 1 | 3 | 5 | 1 | 3 | 5 | 1 | 3 | 5 | 1 | 3 | 5 | 1 | 3 | 5 | 1 | 3 | 5 | 1 | 3 | 5 |

TABLE 4

*Aspergillus niger* ATCC16404 $5.9 \times 10^6$ cfu/ml

| Concentration | Example 1 | | | Example 2 | | | Example 3 | | | Example 4 | | | Example 5 | | | Example 6 | | | Example 7 | | | Comparative Example 4 | | |
|---|---|---|---|---|---|---|---|---|---|---|---|---|---|---|---|---|---|---|---|---|---|---|---|---|
| 0.08% | − | − | − | − | − | − | − | − | − | − | − | − | − | − | − | − | − | − | − | − | − | + | + | + |
| 0.04% | − | − | − | − | − | − | − | − | − | + | − | − | − | − | − | − | − | − | − | − | − | + | + | + |
| Contact time (min) | 1 | 3 | 5 | 1 | 3 | 5 | 1 | 3 | 5 | 1 | 3 | 5 | 1 | 3 | 5 | 1 | 3 | 5 | 1 | 3 | 5 | 1 | 3 | 5 |

Examples 8 to 14

Tabletting Test 2

Tablets were produced by directly tabletting 0.2 g of raw materials mixed according to the formulations shown in Table 5 using a continuous tabletting machine (Piccola B-10, manu- (Dissolution Time)

A tablet was put in 200 ml of water at 20° C., and the time until completion of foaming was measured.

(State of Aqueous Solution)

A tablet was put in 200 ml of water at 20° C., and the state of the aqueous solution was observed after completion of foaming.

TABLE 5

| Ingredient (wt %) | Example 8 | Example 9 | Example 10 | Example 11 | Example 12 | Example 13 | Example 14 |
|---|---|---|---|---|---|---|---|
| Germicidal ingredient A *1 | 25 | 50 | 50 | 50 | 5 | 5 | 4.5 |
| Dextrin | 25 | 48 | 40 | 20 | 5 | 5 | 0 |
| Sodium bicarbonate | 30 | 1 | 5 | 15 | 65 | 80 | 90 |
| Succinic acid (solubility 6.45%) | 20 | 1 | 5 | 15 | 25 | 10 | 5.5 |
| pH (1 wt % aqueous solution) | 6.0 | 6.7 | 6.0 | 5.6 | 6.4 | 6.8 | 7.4 |

*1 Germicidal ingredient A: 1,10-di(3-decyl-2-methylimidazolium)decane dichloride (10-10-10-Cl)

TABLE 6

| | Example 8 | Example 9 | Example 10 | Example 11 | Example 12 | Example 13 | Example 14 |
|---|---|---|---|---|---|---|---|
| Tablet hardness (N) | 36.6 | 44.6 | 45.6 | 93.4 | 48.8 | 53.5 | 44.4 |
| Dissolution time (min:sec) | 4:10 | 110:00 | 95:00 | 21:30 | 3:20 | 3:30 | 2:30 |

TABLE 6-continued

|  | Example 8 | Example 9 | Example 10 | Example 11 | Example 12 | Example 13 | Example 14 |
|---|---|---|---|---|---|---|---|
| State of aqueous solution | clear | clear | clear | clear | clear, with a few undissolved residues (which were completely dissolved by stirring) | clear; about one-quarter of tablet remains undissolved (which was completely dissolved by stirring) | clear; about three-quarters of tablet remain undissolved (which were completely dissolved by stirring) |

Test Examples 1 and 2

Test for Inhibition of Drug Resistance Development

According to the standard method (broth microdilution method) of Japanese Society of Chemotherapy, minimal inhibitory concentration (MIC) was continuously measured. The compositions shown in Table 7 were diluted with sterile water to obtain drug solutions with a concentration of the composition of 0.007 to 1.792% by weight, and a nutrient broth medium adjusted to a concentration twice as high as the specified concentration (manufactured by Eiken Chemical Co., Ltd., normal bouillon medium 'Eiken' E-MC35) was added thereto in an amount equal to the drug solution. The obtained mixture was stirred and then dispensed to a microtiter plate (96 well) in an amount of 150 µl/well. Next, each of the following sample bacteria isolated from a food factory was cultured in an NB medium at 30° C. for 20 hours, and the obtained culture was diluted with a physiological saline solution to the concentration of $10^7$ cfu/ml. The diluted culture was then seeded in an amount of 7.5 µl/well to the microtiter plate containing the medium prepared as described above. The plate was incubated in a constant temperature oven at 30° C. for 48 hours, the growth of the bacterium was checked by visual inspection, and MIC was determined. Further, the culture was collected from a well with a maximum drug concentration among wells in which growth was confirmed, and diluted with a physiological saline solution to the concentration of $10^7$ cfu/ml. Using the diluted culture, MIC was determined again in the same manner as described above. MIC was determined eight times in total by repeating the above procedure, and changes in MIC were confirmed.

Sample Bacterium (iii): *Serratia marcescens* (Bacterium 2 Isolated from a Food Factory)

Sample Bacterium (iv): *Serratia marcescens* (Bacterium 3 Isolated from a Food Factory)

TABLE 7

| Ingredient (wt %) | Test Example 1 | Test Example 2 |
|---|---|---|
| Germicidal ingredient A *1 | 9 | 0 |
| DDAC *2 | 0 | 9 |
| Triethanolamine | 0.13 | 0 |
| Water | 90.87 | 91 |
| pH | 9.0 | 8.7 |

*1 Germicidal ingredient A: 1,10-di(3-decyl-2-methylimidazolium)decane dichloride
*2 DDAC: didecyl dimethyl ammonium chloride The results are shown in Tables 8 and 9. With respect to the composition of Test Example 1, the MIC was low even at the eighth round, which was 0.056% by weight (for the sample bacterium (iii)) and 0.028% by weight (for the sample bacterium (iv)). It was confirmed that drug-resistant microorganisms have hardly developed when using the compound of the formula (I) [1,10-di(3-decyl-2-methylimidazolium)decane dichloride] as compared to the case where DDAC is used.

TABLE 8

Proliferation of *Serratia marcescens*
(bacterium 2 isolated from a food factory)

| Concentration (wt %) | Test Example 1 | | | | | | | | Test Example 2 | | | | | | | |
|---|---|---|---|---|---|---|---|---|---|---|---|---|---|---|---|---|
| 0.896 | − | − | − | − | − | − | − | − | − | − | − | + | + | + | + | + |
| 0.448 | − | − | − | − | − | − | − | − | − | − | − | + | + | + | + | + |
| 0.224 | − | − | − | − | − | − | − | − | − | − | + | + | + | + | + | + |
| 0.112 | − | − | − | − | − | − | − | − | − | − | + | + | + | + | + | + |
| 0.056 | − | − | − | − | − | − | − | + | + | + | + | + | + | + | + | + |
| 0.028 | − | − | − | − | − | + | + | + | + | + | + | + | + | + | + | + |
| 0.014 | − | − | − | − | + | + | + | + | + | + | + | + | + | + | + | + |
| 0.007 | + | + | + | + | + | + | + | + | + | + | + | + | + | + | + | + |
| 0.0035 | + | + | + | + | + | + | + | + | + | + | + | + | + | + | + | + |
| Test round | 1 | 2 | 3 | 4 | 5 | 6 | 7 | 8 | 1 | 2 | 3 | 4 | 5 | 6 | 7 | 8 |

TABLE 9

Proliferation of *Serratia marcescens*
(bacterium 3 isolated from a food factory)

| Concentration (wt %) | Test Example 1 | | | | | | | | Test Example 2 | | | | | | | |
|---|---|---|---|---|---|---|---|---|---|---|---|---|---|---|---|---|
| 0.896 | − | − | − | − | − | − | − | − | + | + | + | + | + | + | + | + |
| 0.448 | − | − | − | − | − | − | − | − | + | + | + | + | + | + | + | + |
| 0.224 | − | − | − | − | − | − | − | − | + | + | + | + | + | + | + | + |
| 0.112 | − | − | − | − | − | − | − | − | + | + | + | + | + | + | + | + |
| 0.056 | − | − | − | − | − | − | − | + | + | + | + | + | + | + | + | + |
| 0.028 | − | − | − | − | − | − | − | − | + | + | + | + | + | + | + | + |
| 0.014 | − | − | − | − | + | + | + | + | + | + | + | + | + | + | + | + |
| 0.007 | + | + | + | + | + | + | + | + | + | + | + | + | + | + | + | + |
| 0.0035 | + | + | + | + | + | + | + | + | + | + | + | + | + | + | + | + |
| Test round | 1 | 2 | 3 | 4 | 5 | 6 | 7 | 8 | 1 | 2 | 3 | 4 | 5 | 6 | 7 | 8 |

What is claimed is:

1. A solid germicidal composition, comprising a compound of the formula (I), a carbonate compound and an organic acid with a solubility in water at 20° C. of 0.25 to 35%:

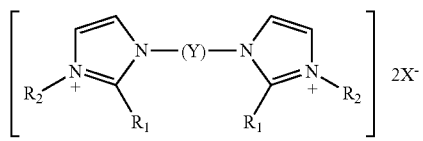

(I)

wherein, $R_1$ represents a saturated linear alkyl group having 1 to 3 carbon atoms, $R_2$ represents a saturated linear alkyl group having 8 to 12 carbon atoms, $X^-$ represents a halogen ion and Y represents a saturated linear alkylene group having 8 to 12 carbon atoms.

2. The composition according to claim 1, wherein the compound of the formula (I) is one or more compounds selected from the group consisting of 1,10-di(3-decyl-2-methylimidazolium)decane dichloride, 1,10-di(3-decyl-2-methylimidazolium)decane dibromide, 1,12-di(3-decyl-2-methylimidazolium)dodecane dichloride and 1,12-di(3-octyl-2-methylimidazolium)dodecane dichloride.

3. The composition according to claim 1, wherein the compound of the formula (I) is 1,10-di(3-decyl-2-methylimidazolium)decane dichloride.

4. The composition according to claim 1, which comprises 0.05 to 18 parts by weight of the carbonate compound relative to 1 part by weight of the compound of the formula (I).

5. The composition according to claim 1, which comprises 0.05 to 18 parts by weight of the organic acid with a solubility in water at 20° C. of 0.25 to 35% relative to 1 part by weight of the compound of the formula (I).

6. The composition according to claim 1, wherein the carbonate compound is sodium bicarbonate or sodium carbonate.

7. The composition according to claim 1, wherein the organic acid is succinic acid or adipic acid.

8. An aqueous solution of the composition according to claim 1.

9. A method for disinfecting an object, which comprises contacting an aqueous solution of the composition according to claim 1 with the object.

10. The method according to claim 9, wherein the object is an object in or on which microorganisms resistant to quaternary ammonium salts and/or biguanide germicides exist or an object to which quaternary ammonium salts and/or biguanide germicides are being applied or were previously applied.

* * * * *